United States Patent [19]

Flammini et al.

[11] Patent Number: 5,625,116
[45] Date of Patent: Apr. 29, 1997

[54] PROCESS FOR THE REMOVAL OF CARBON MONOXIDE FROM ALPHA-OLEFINS AND SATURATED HYDROCARBONS

[75] Inventors: Roberto Flammini, Piazzale San Benedetto; Giovanni Patroncini, Via Ferrariola, both of Italy

[73] Assignee: Montell North America Inc., Wilmington, Del.

[21] Appl. No.: 457,720

[22] Filed: Jun. 1, 1995

Related U.S. Application Data

[63] Continuation of Ser. No. 958,386, Oct. 8, 1992, abandoned.

[30] Foreign Application Priority Data

Oct. 8, 1991 [IT] Italy ................... MI91A2666

[51] Int. Cl.$^6$ .................. C07C 7/148; C07C 7/152
[52] U.S. Cl. .................. 585/848; 585/845; 585/850; 585/855; 423/247
[58] Field of Search ................... 585/845, 848, 585/850, 855; 423/247

[56] References Cited

U.S. PATENT DOCUMENTS

| | | | |
|---|---|---|---|
| 3,676,516 | 7/1972 | Haskell et al. | 585/848 |
| 3,787,322 | 1/1974 | Koberstein et al. | 502/318 |
| 3,855,388 | 12/1974 | Rosinski | 502/318 |
| 4,185,039 | 1/1980 | Eden | 585/848 |
| 5,045,297 | 9/1991 | Bonifaz et al. | 423/247 |

FOREIGN PATENT DOCUMENTS

| | | |
|---|---|---|
| 55-154921 | 12/1980 | Japan. |
| 886893 | 1/1962 | United Kingdom. |

OTHER PUBLICATIONS

Handbook of Chemistry and Physics, (30th Ed, 1947, pp. 1808 & 2315).

*Primary Examiner*—Helane Myers
*Assistant Examiner*—In Suk Bullock

[57] ABSTRACT

The carbon monoxide contained in α-olefins and saturated hydrocarbons, in particular α-olefins and $C_{2-4}$ saturated hydrocarbons, is removed, by contacting such α-olefins and saturated hydrocarbons, at a temperature ranging from 0° to 150° C., with a catalyst system comprising a mixture and/or the reaction product of:

A) one or more oxides of metals selected from the group consisting of Cu, Fe, Ni, Co, Pt, Pd; and B) one or more oxides of metals selected from the group consisting of metals of groups V B, VI B, or VII B of the Periodic Table;

thus reducing the content of carbon monoxide to values lower than 0.03 ppm.

3 Claims, No Drawings

PROCESS FOR THE REMOVAL OF CARBON MONOXIDE FROM ALPHA-OLEFINS AND SATURATED HYDROCARBONS

FIELD OF THE INVENTION

This application is a continuation, of application Ser. No. 07/958,386, filed Oct. 8, 1992, now abandoned.

The present invention concerns a process for the removal of carbon monoxide from α-olefins and saturated hydrocarbons, in order to make said α-olefins and saturated hydrocarbons suitable for use in Ziegler-Natta polymerization processes. In particular, the process of the present invention can be used advantageously for the purification of $C_{2-4}$ α-olefins obtained by way of thermal cracking processes, which constitute the primary production source of said α-olefins.

BACKGROUND OF THE INVENTION

It is known that α-olefins obtained by thermal cracking of mineral oils, even after complex separation and refining treatments, contain small quantities of impurities, many of which, carbon monoxide included, have a detrimental effect on the Ziegler-Natta catalysts, particularly the high-yield catalysts, which generally contain a halogenated titanium halide compound supported on magnesium chloride, and an aluminum alkyl compound as the co-catalyst.

The carbon monoxide is generally present in the above mentioned α-olefins in a quantity ranging from 0.5 to 10 ppm (hereinafter understood to be ppm in moles), and at such levels it reduces considerably the efficiency of the Ziegler-Natta catalysts. On the other hand, it is not easy to further reduce the above mentioned concentrations of carbon monoxide in $C_{2-4}$ α-olefins by simple distillation, given the low boiling point of said α-olefins. In particular, when the concentration of carbon monoxide is lower than or equal to 2 ppm, distillation becomes remarkably burdensome even from an economic standpoint.

The economic damage which derives from the presence of carbon monoxide in a polymerization process can be even worse when, as it often happens, the concentration of carbon monoxide fluctuates within the above mentioned range, thus causing a similar fluctuation of the polymer yield at the point where the latter exits the polymerization reactors, and this forces one to undertake continuous and costly operations to adjust the catalyst feeding systems, and not always with positive results. This proves how important it is to reduce the concentration of carbon monoxide in the α-olefins to levels below 0.03 ppm, where the influence on the behavior of the Ziegler-Natta catalysts is negligible.

The methods used up to date to reduce said carbon monoxide content in the α-olefins obtained by refining mineral oils (including thermal cracking), consist of using the capacity of some transition metal compounds, in particular copper compounds, in an aqueous solution form, or dispersed on inert solid supports (such as alumina or silica), to form complexes with the carbon monoxide.

For example, according to U.S. Pat. No. 3,014,973, the α-olefins to be purified, in particular ethylene and propylene, are absorbed in aqueous cuproammonium solutions, and subsequently selectively desorbed in such a way as to separate them from the carbon monoxide which remains complexed with the copper compound.

In order to further lower the carbon monoxide content, an additional treatment of the α-olefins by way of contacting them with the hydroxide of an alkali metal at temperatures higher than 170° C. is expected.

From the data shown in U.S. Pat. No. 3,014,973, it is not obvious if by using the above mentioned process it is possible to reduce the concentration of carbon monoxide to less than 0.03 ppm. However, the above process is complex and costly, and requires an additional liquefying stage of the purified olefin, whenever, as it often happens in the case of propylene and 1-butene, one wants to carry out the polymerization in liquid monomer.

SUMMARY OF THE INVENTION

The process for removing carbon monoxide from α-olefins and saturated hydrocarbons according to the present invention comprises contacting the α-olefin, or saturated hydrocarbon, containing the carbon monoxide, at temperatures ranging from 0° to 150° C. preferably from 20° to 95° C., with a catalyst system comprising a mixture and/or reaction product of:

A) one or more oxides of metals selected from the group consisting of Cu, Fe, Ni, Co, Pt, and Pd; and B) one or more oxides of metals selected from the group consisting of metals of groups V B, VI B, or VII B of the Periodic Table.

DETAILED DESCRIPTION

The process of the present invention provides for the removal of carbon monoxide from α-olefins, which allows operation in a particularly simple and effective manner, at low temperatures, and maintaining the α-olefins, particularly propylene and 1-butene, in the liquid state.

Moreover, the same process can be used also for the removal of carbon monoxide from saturated hydrocarbons such as ethane, propane and butane, which may be present as diluents in the polymerization of α-olefins. As for the α-olefins, the problem of the presence of carbon monoxide is particularly serious in the case of light saturated hydrocarbons, particularly $C_{2-4}$, which, given the low boiling point, present difficulties when the carbon monoxide is removed by distillation.

As previously stated, the process of the present invention allows one to reduce the content of carbon monoxide in α-olefins and saturated hydrocarbons until the concentration falls below 0.03 ppm, particularly until the concentration goes below 0.02 ppm.

In the case of propylene, 1-butene, and easily liquefiable saturated hydrocarbons, the operation is carried out preferably in the liquid state.

Although it is not meant for the operation mechanism to limit the present invention, it has been found that the above catalyst systems, including the mixture and/or the reaction product of (A)+(B), are oxidizing catalyst systems, and therefore, they are capable of transforming the carbon monoxide present in the α-olefin or saturated hydrocarbon into carbon dioxide.

Since the levels above which carbon dioxide can influence the activity of the Ziegler-Natta catalysts are considerably higher that those of carbon monoxide, and usually higher than 5 ppm, the presence in quantities up to 5 ppm of carbon dioxide which replaces the carbon monoxide in the α-olefins and saturated hydrocarbons purified with the process of the present invention, does not generally lead to polymerization problems.

The initial concentration levels of carbon monoxide within which the process of the present invention can be used most advantageously, therefore, are those that are lower than or equal to about 5 ppm, particularly from 0.5 to 5 ppm.

If necessary, the content of carbon dioxide in the α-olefins and saturated hydrocarbons can easily be reduced to contents lower than or equal to 5 ppm, by contacting, according to technical reports, with alkali metal hydroxides, particularly Na or K, optionally supported on inert supports, such as calcium carbonate or activated carbon. It is possible, for example, to make the α-olefins or saturated hydrocarbons flow on fixed beds containing the above mentioned hydroxides in the solid state and homogeneously distributed; in this manner, the carbon dioxide is fixed as carbonate.

Among the catalyst systems used in the process of this invention, particularly preferred are the ones where component (A) comprises or is made up of copper oxide (CuO); for component (B) the preferred catalyst systems are the ones where said component comprises or is made up of an oxide of a metal selected from the group consisting of V; Nb; Cr; Mo; W. Particularly preferred for component (B) is chromium oxide ($Cr_2O_3$).

Depending on the preparation method, the catalyst systems can also comprise reaction products of oxides (A) and (B). For example, a catalyst system obtained from CuO and $Cr_2O_3$ can comprise or be made up of $CuCr_2O_4$.

Components (A) and (B), as a mixture or as products of a reaction between them, are generally present, in the catalyst system used according to this invention, in molar ratios (A):(B) ranging from 1:10 to 10:1, preferably from 1:2 to 5:1. Particularly preferred are the catalyst systems comprising CuO and $Cr_2O_3$, as such and/or as $CuCr_2O_4$, in the above mentioned proportions.

The catalyst systems used in the process of this invention can also be supported on inert supports such as silica, alumina, diatomaceous earth, and activated carbon.

The methods for preparation of the above mentioned catalyst systems vary mainly depending on the desired chemical composition and morphology.

By way of example, it is possible to operate by mixing the (A) and (B) oxides, by co-milling for example, or by thermal decomposition of mixtures of various compounds of the respective metals, which can be converted into oxides by way of such thermal decomposition.

The compounds that can be converted into oxides by way of thermal decomposition are generally selected from the organic and inorganic acid salts, such as for example alcoholates, nitrates or carbonates. Said salts can also be used in solution in appropriate solvents, preferably in water, for the purpose of impregnating the above mentioned inert supports, thus obtaining, by evaporation of the solvent and subsequent thermal decomposition, supported catalyst systems. The thermal decomposition is appropriately carried out by way of heating at a temperature generally ranging from 150° to 800° C. in the presence of air or oxygen.

Some of the above mentioned catalyst systems are normally used in the reduced state, i.e., after having been treated with hydrogen, as hydrogenation-dehydrogenation or hydration catalysts in various organic syntheses. They are available commercially.

Contrary to the above mentioned application methods after hydrogen treatment, in the process of the present invention the catalyst systems described above are used as such, or after treatment in air or oxygen flow generally at temperatures ranging from 80° C. and 500° C. and time spans ranging from 1 to 100 hours.

Examples of catalyst systems commercially available which can be used advantageously in the process of the present invention, are the Cu-0203T and Cu-1230E types, produced by ENGELHARD. The catalyst Cu 0203 T contains CuO and $Cr_2O_3$ in quantities by weight equal to 79% and 17% respectively. The catalyst Cu 1230 E contains CuO and $Cr_2O_3$ in quantities by weight equal to 30% and 31% respectively, and is supported on alumina. It is believed that a part of the oxides in these is in the form of $CuCr_2O_4$.

The α-olefins and saturated hydrocarbons containing carbon monoxide are preferably contacted in the liquid state with the catalyst systems comprising the mixture and/or the reaction product of (A)+(B).

The operating pressure generally used is that necessary to maintain the α-olefin or saturated hydrocarbon in the liquid state, corresponding to the process temperature used. For example, in the case of propylene or 1-butene, the operation usually takes place at a pressure ranging from 1 to 200 atm, preferably from 2 to 50 atm.

In the event that it is not necessary for the polymerization to liquify the α-olefin or saturated hydrocarbon, the α-olefin or saturated hydrocarbon may be contacted with the catalyst system while in the gaseous state. In this case one preferably operates at pressures ranging from 20 to 100 atm.

According to the process of the present invention, the catalyst systems described above are generally used in the form of dispersed particles placed on fixed or stirred beds. The average diameter of the particles ranges preferably from 500 to 10,000 μm.

The α-olefins or saturated hydrocarbons to be purified are caused to flow on the above mentioned catalyst beds at a space velocity generally ranging from 2 to 20 $h^{-1}$. The operation is generally continuous, and lasts anywhere from 10 to 500 hrs, preferably from 40 to 250 hrs. Said time periods correspond to the life of the catalyst system, i.e., the period of time during which the catalyst system maintains a satisfactory level of efficiency in the removal of the carbon monoxide, depending mainly on: the chemical composition, and the physical and morphological structure of the catalyst system used; the conditions of use; and the content of carbon monoxide and other impurities present in the α-olefins and saturated hydrocarbons to be purified.

By operating under the above mentioned conditions, one can remove quantities of carbon monoxide equal to approximately 1 Kg of CO per 100 Kg of catalyst system, thus purifying liquid propylene containing 1–3 ppm of carbon monoxide.

An additional advantage of the process of the present invention is that the previously mentioned catalyst system can be regenerated and reutilized.

The regeneration is generally carried out by heating the catalyst system in air or oxygen, to 80°–500° C., preferably to 150°–200° C. for 1–100 hrs, preferably for 4–30 hrs.

The following examples are given in order to illustrate, but not limit, the present invention.

In all the examples the concentrations of CO and $CO_2$ are determined by way of gas-chromatographic analysis.

CONTROL EXAMPLE 1

In order to verify the efficiency of the catalyst system in the removal of carbon monoxide from liquid propylene, a test was carried out at a high concentration of carbon monoxide using the following methods.

In a 1.8 l stainless steel autoclave equipped with agitator and a silicone oil heating device, in nitrogen atmosphere, are introduced 50 g of ENGELHARD Cu 1230 E $1/16$-3F catalyst, previously activated by way of air flow treatment at 170° C. for 4 hours. 676 g of liquid propylene containing 1500 ppm of carbon monoxide and about 2 ppm of $CO_2$ are then added.

The autoclave is maintained under agitation for 6.5 hours at 44° C., and for 15.5 hours at 31° C., after which a sample of liquid propylene is taken. The gas-chromatographic analysis carried out on said sample shows a CO and $CO_2$ content of 660 ppm and 816 ppm respectively, thus proving that the CO has been quantitatively transformed into $CO_2$.

CONTROL EXAMPLE 2

Example 1 is repeated, but in this case the propylene used has a CO content equal to 1800 ppm, and about 2 ppm of $CO_2$, and the autoclave is maintained at a temperature ranging from 42° to 47° C. for 21 hours. The final CO content is 640 ppm, showing again that the CO was quantitatively transformed into $CO_2$.

CONTROL EXAMPLE 3

(comparative)

Control Example 1 is repeated, but in this case the propylene used has a content of CO equal to 1300 ppm and about 2 ppm of $CO_2$, and 50 g of ENGELHARD B 038A-006-06-T ⅛ catalyst are added while maintaining the autoclave at 45° C. for 31 hours.

The above catalyst is essentially made up of CuO supported on silica.

The final CO content is 1200 ppm., thus showing that a catalyst which is solely based on copper oxide is not effective in the removal of carbon monoxide from liquid propylene.

EXAMPLE 4

The same catalyst used in Control Example 1 is used in a series of three tests for the purification of liquid propylene containing a quantity of CO included within the limits commonly found in "polymerization grade" industrially produced propylene.

The apparatus used comprises a 20 l stainless steel vessel equipped with feed pipes used to introduce into the vessel liquid propylene, CO and nitrogen (necessary to maintain a constant pressure of the liquid propylene).

At the bottom of the vessel is a sampling device for the analysis of the initial CO content, and a tube for the discharge of the propylene to be purified. Said discharge tube is connected to the lower part of the purifier by way of a water/steam preheater. The purifier is made up of a stainless steel cylinder with a 50 mm inside diameter and a height of 500 mm, equipped at both ends with discs and screen filters to prevent the catalyst from escaping. The cylinder, with the catalyst in place, is heated to the desired temperature by water/steam circulating in an outside jacket.

The propylene which enters from the bottom comes in contact with the catalyst for the desired length of time, and exits purified from the top of the cylinder; before being discharged, a sampling device allows regular removal of samples to be analyzed for the final CO content.

659 g of catalyst were used in all the tests. The principal operating parameters, as well as initial and final concentrations of CO, are shown in Table 1.

EXAMPLE 5

Three liquid propylene purification tests are carried out by using the same apparatus of Example 4, and using, in all the tests, 325 g of ENGELHARD Cu-0203 T ⅛" catalyst.

The principal operating parameters, as well as initial and final concentrations of CO are shown in Table 1.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

TABLE 1

| Test no. | T (°C.) | P (atm) | Time (hrs) | $C_3$ (1/hr) | $CO^1$ (ppm) | $CO^2$ (ppm) | Resid. Time | LHSV (hrs$^{-1}$) |
| --- | --- | --- | --- | --- | --- | --- | --- | --- |
| Example 4 | | | | | | | | |
| 1 | 44 | 20 | 15 | 1.6 | 1.16 | <0.03 | 26 | 2.3 |
| 2 | 44 | 20 | 58 | 4 | 3.6 | <0.03 | 10.5 | 5.7 |
| 3 | 44 | 20 | 62.5 | 4 | 2.3 | <0.03 | 7.5 | 8 |
| Example 5 | | | | | | | | |
| 1 | 45 | 19 | 18 | 0.78 | 3.21 | 0.006 | 13.46 | 4.457 |
| 2 | 45 | 19 | 24.5 | 0.79 | 1.81 | 0.025 | 13.29 | 4.514 |
| 3 | 45 | 19 | 42 | 0.84 | 3.82 | 0.02 | 12.5 | 4.800 |

Notes for Table 1
P = feeding pressure
$C_3$ = propylene being fed
$CO^1$ = initial concentration of CO
$CO^2$ = final concentration of CO
Resid. Time = Residence time
LHSV = Space velocity

We claim:

1. Process for removing carbon monoxide from a liquid hydrocarbon containing 0.5 to 5 ppm by moles of carbon monoxide, said hydrocarbon being selected from the group consisting of propylene, 1-butene, ethane, propane, butane, and mixtures thereof, said process comprising contacting said hydrocarbon at a temperature in the range from 0° C. to 150° C., and at a pressure at which said hydrocarbon is maintained in the liquid state, with a catalyst system comprising a mixture or a reaction product or both of CuO and $Cr_2O_3$, the molar ratio of CuO to $Cr_2O_3$ being from 1:10 to 10:1, said catalyst system having been preheated in air or oxygen at 80°–500° C. for 1–100 hours.

2. Process of claim 1, wherein said catalyst system contains $CuCr_2O_4$.

3. Process of claim 1 wherein said temperature is in the range from 20° to 95° C.

* * * * *